(12) United States Patent
Bertling

(10) Patent No.: US 6,187,589 B1
(45) Date of Patent: Feb. 13, 2001

(54) VECTORIAL CLONING SYSTEM OF DNA

(75) Inventor: Wolf Bertling, Erlangen (DE)

(73) Assignee: November AB Novus Medicatus Berling Gesellschaft fur Molekulare Medizin (DE)

( * ) Notice: Under 35 U.S.C. 154(b), the term of this patent shall be extended for 0 days.

(21) Appl. No.: 09/331,362

(22) PCT Filed: Dec. 18, 1997

(86) PCT No.: PCT/DE97/02963

§ 371 Date: Oct. 5, 1999

§ 102(e) Date: Oct. 5, 1999

(87) PCT Pub. No.: WO98/28415

PCT Pub. Date: Jul. 2, 1998

(30) Foreign Application Priority Data

Dec. 20, 1996 (DE) .............................................. 196 53 498

(51) Int. Cl.[7] .................................................. C12N 15/63
(52) U.S. Cl. .................. 435/476; 435/199; 435/320.1
(58) Field of Search ................................ 435/320.1, 476, 435/199

(56) References Cited

U.S. PATENT DOCUMENTS 5,196,524    3/1993    Gusatfson et al. .................. 536/23.2
5,434,063  * 7/1995    Lacks .................................. 435/91.1

FOREIGN PATENT DOCUMENTS

| 0161937 | * 11/1984 | (EP) . |
| 0293249 | * 11/1988 | (EP) . |
| 0 466 332 A2 | 1/1992 | (EP) . |
| 0532043 | * 3/1993 | (EP) . |
| 2212160 | 7/1989 | (GB) . |

OTHER PUBLICATIONS

Cease, K.B., et al. (1993) Biotech. 14(2), 250–252, 254–255.*
Kong, H.K., et al. (1994) J. Biol. Chem. 269(1), 683–690.*
Markmeyer, P., et al. (1990) Gene 93, 129–134.*

* cited by examiner

Primary Examiner—Charles L. Patterson, Jr.
(74) Attorney, Agent, or Firm—Fish & Richardson P.C., P.A.

(57) ABSTRACT

The invention relates to a vectorial cloning system consisting of a sequence of nucleotides, containing a fusion sequence and one or several restriction endonucleases, recognition sites for restriction endonucleases cutting outside their recognition sites, in addition to containing one or several other restriction endonuclease recognition sites which can be used to clone a foreign protein as well as the sequence for the desired foreign protein, wherein the foreign protein sequence is directly located on the fusion sequence after a subsequent restriction with the restriction endonucleases, followed by religation.

10 Claims, 3 Drawing Sheets

```
        SfiI         RsrII                                                   BcgI           HincII
5'CAC GGA TCA ATC GAA GGA CGC ATC AGC CTG GTC CGA GCT GAG TGC AGT CGA CCG CAT GCG AGC TCG GTA CC  (SEQ ID NO:2)
3'GTG CCT AGT CTT CCG GCG TAG TCG GAC CAG GCT CGA CTC ACG TCA GCT GGC GTA CGC TCG AGC CAT GG     (SEQ ID NO:3)
   His Gly Ser Ile Glu Gly Arg                                                   SphI  SacI  KpnI
                            Xa
```

FIG. 1

```
        SfiI         RsrII                                                   BcgI         HincII
5'CAC GGA TCA ATC GAA GGA CGC ATC AGC CTG GTC CGA GCT GAG TGC AGT CGG CCG CAT | GNN NNN  (SEQ ID NO:4)
3'GTG CCT AGT TAG CTT CCG GCG TAG TCG GAC CAG GCT CGA CTC ACG TCA GCC GGC G | TA CNN NNN
   His Gly Ser Ile Glu Gly Arg                                                      (NotI)
                            Xa
```

FIG. 2

```
        SfiI         RsrII                                                   BcgI         HincII
5'CAC GGA TCA ATC GAA GGA CGC AT | C AGC CTG GTC CGA GCT GAG TGC AGT CGG ATC CAT | GNN NNN  (SEQ ID NO:5)
3'GTG CCT AGT TAG CTT CCG GCG | TAG TCG GAC CAG GCT CGA CTC ACG TCA GCC TAG G | TA CNN NNN
   His Gly Ser Ile Glu Gly Arg                                                     (BamHI)
                            Xa
```

FIG. 3

```
         SfiI           RsrII
5' CAC GGA TCA ATC GAA GGA CGC ATIC ACC CTC CTC CGA CCT CAC TGC AGT CGA CGA TAT| GNN NNN  (SEQ. ID NO:6)
3' GTG CCT AGT TAG CTC CCG GCG |TAG TCG GAC GAG GCT CGA CTC ACG TCA GCT TAG A|TA CNN NNN
   His Gly Ser Ile Glu Gly Arg                                       (HincII)
                                                          BcgI              (ClaI)
```

FIG. 4

```
         SfiI           RsrII
5' CAT CAC CAT CAC CAT CAC GGA TCA ATC GAA GGA CGC ATG NNN   (SEQ ID NO:7)
3' GTA GTG GTA GTG GTA GTG CCT AGT TAG CTC CCG GCG TAC NNN
   His His His His His His Gly Ser Ile Glu Gly Arg|Met       (SEQ ID NO:8)
                                                  Xa
```

FIG. 5

```
5' CAT CAC CAT CAC CAT CAC GGA TCA ATC GAA GGA CGC   (SEQ ID NO:9)
3' GTA GTG GTA GTG GTA GTG CCT AGT TAG CTC CCG GCG
   His His His His His His Gly Ser Ile Glu Gly Arg  (SEQ ID NO:10)
                                                  Xa
```

FIG. 6

```
        SfiI           RsrII
5' CAC GGA TCA ATC GAA GGA CGC ATlC AGC CTG GTC CGA GGT GAG TGC AGT CGA CCG CAT | GCG AGC TCG GTA CC      (SEQ ID NO:11)
3' GTG CCT AGT TAG CTT CCT GCG GCG |TAG TCG AGC CAG CCT CGA CTC ACG TCA GCT GGC G | TA CGC TCG AGC CAT GG
   His Gly Ser Ile Glu Gly Arg (SEQ ID NO:3)
                           Xa                                  BcgI       HincII       SphI    SacI    KpnI
```

FIG. 7

VECTORIAL CLONING SYSTEM OF DNA

The invention relates to a vector system for cloning.

As a rule, common vectors which are used for cloning in prokaryotic systems contain the following features: a selection gene, e.g. the gene encoding resistance to ampicillin, a marker gene which makes it possible, e.g. on the basis of a color reaction, as in the case of the lacZ gene, to distinguish vectors with and without insert, and, especially, an origin of replication. The reader is also referred to the following documents with regard to the state of the art:

a) EP 0 532 043 A2,
b) EP 0 466 332 A2,
c) EP 0 293 249 A1,
d) GB 22 12 160 A and
e) U.S. Pat. No. 51 96 524.

The vector system described in publication c consists of a sequence of nucleotides which codes for the expression of a fusion protein. However, the foreign protein sequence in this case is linked directly to the sequence for an enzyme and is not separated by additional structures during the cloning process.

In systems which are based on phages rather than plasmids, further genetic elements are included which are important for the functions of the life cycle of the phage. Cleavage sites which occur only a few times in the vector, preferably only once, are normally used in these systems for inserting a foreign sequence into a marker gene. A series of such cleavage sites is normally arranged in a so-called multiple cloning site. Further elements, apart from this multiple cloning site, are included in some vectors which are used for expressing foreign proteins. In some genes, use is made, for this purpose, of a sequence which results, together with the insert to be cloned, in a fusion protein which then has an affinity for, e.g., maltose residues or nickel chelates. In some cases, these residues are joined by a recognition sequence for a proteinase, e.g. factor Xa. After purification by means of affinity chromatography has been effected, these proteinase cleavage sites make it possible to cleave the fusion protein into the affinity moiety and the foreign protein which is actually to be expressed. Since, however, this proteinase cleavage site is as a rule followed by a multiple cloning site sequence into which the sequence to be expressed has been cloned, additional, frequently unwanted amino acids remain on the foreign protein to be expressed after the fusion protein has been subjected to the processing with proteinase.

Most foreign protein sequences which are to be expressed are present in a nucleic acid environment which does not allow direct cloning directly after an endoproteinase recognition sequence to be effected efficiently using current cloning strategies. Using a multiple cloning site immediately after the endoproteinase recognition sequence (i.e. 3' of the endoproteinase recognition sequence) markedly facilitates cloning of foreign protein sequences which are to be expressed. In this connection, it is disadvantageous that, at the protein level, it is not the foreign protein to be expressed which is recovered following digestion with the enzyme which recognizes the corresponding protein sequence; instead, that which is recovered is a fusion protein which comprises the foreign protein sequence to be expressed together with additional amino acids which are encoded by the residues of the multiple cloning site.

The object of the invention is to provide a novel vector system for cloning foreign proteins which avoids the disadvantages of the state of the art. This object is achieved by the features of claims 1 and 10. Advantageous embodiments ensue from the features of claims 2–9 and 11.

Use of the cloning vector system which is presented here now makes it possible, in a subsequent digestion and religation step, to bring the foreign protein sequence to be expressed directly up against an endoproteinase recognition sequence. This ensures that, after digestion with the enzyme which recognizes the corresponding protein sequence, the foreign protein sequence to be expressed is released, without any further components, from an expressed fusion protein.

A particular advantage is also to be seen in the fact that it is possible to select the reading frame at will during the process which is presented here. This makes it possible not only to exactly position the foreign gene component to be expressed but also to define the start of the fusion gene component. The following strategy was selective for preventing, in a simple but nevertheless highly selective manner, the unwanted expression, occasioned by the cloning procedure, of additional peptide components on the foreign gene to be expressed:

Use was made of the recognition sequence for the enzyme BcgI in order to clone it within the multiple cloning site, into which the foreign sequence can subsequently be inserted using any arbitrary enzymes. BcgI is one of the enzymes, so far the only one which is commercially available, which cleave both upstream and downstream of their recognition sequence at a defined distance (10/12 nucleotides) from this sequence.

This cleavage by the enzyme consequently removes a sequence segment of $2 \times 6 + 10 + 12 = 34$ bp. Subsequent religation consequently generates sequences from which 34 base pairs have been removed. Consequently, if a specific cloning has been carried out, the last nucleotide of the endoproteinase recognition sequence and the first nucleotide of the first codon of the protein to be cloned, for example, then lie directly adjacent. Examples of sequences are given in Example 1 in association with a listing of some applications.

Particular advantages of the BcgI system include its tendency to lead in 10–50% of cases, depending on the buffer concentration, to small deletions (3 nucleotides as a rule) at the cleavage site. This then results, in these cases, in the first amino acid of the foreign protein to be expressed, as a rule methionine, no longer being a constituent of the foreign protein, which is to be expressed and which is released, after digestion with the enzyme which recognizes the corresponding protein sequence.

A similar result is obtained when two restriction endonuclease recognition sites are used; i.e. with one of the sites being in, or in the immediate vicinity of, the region of an endoproteinase recognition sequence and the other recognition site, which is ligation-compatible with the former, being located directly upstream of the foreign protein sequence to be expressed such that digestion with the corresponding restriction endonuclease and subsequent religation brings the beginning of the foreign protein sequence to be expressed directly up against the endoproteinase recognition sequence.

The invention is explained below with the aid of some sequences and examples.

FIG. 1 shows a first sequence,

FIG. 2 shows a second sequence of the multiple cloning site,

FIG. 3 shows a third sequence using BamHI as an example,

FIG. 4 shows a fourth sequence using ClaI as an example,

FIG. 5 shows one of the preceding sequences following restriction and religation, FIG. 6 shows a fifth sequence, namely a fusion sequence, and FIG. 7 shows a sixth sequence which contains a BcgI recognition site.

The first sequence, shown in FIG. 1, permits cloning in all three reading frames.

1. If, for example, a Not I or AscI recognition site is located directly upstream of the ATG of a foreign gene to be expressed, this enzyme can be used and the fragment can be filled in to give a blunt end and cloned on to the starting construct which has been cut with HincII. This is shown in FIG. 2.

2. If, for example, any arbitrary restriction recognition site which generates a 4-nucleotide 3'-overhanging end is located directly upstream of the ATG of a foreign gene to be expressed, this enzyme can then be used, and the fragment can be filled in to give a blunt end and cloned on to the starting construct which has been cut with AccI and as likewise been filled in. This is shown in FIG. 3 using BamHI as an example.

3. If, for example, any arbitrary restriction recognition site which generates a 2-nucleotide 3'-overhanging end is located directly upstream of the ATG of a foreign gene to be expressed, this enzyme can then be used and the fragment can be filled in to give a blunt end and cloned on to the starting construct which has been cut with SalI and is likewise been filled in. This is shown in FIG. 4 using ClaI as an example.

Subsequent restriction with BcgI and religation gives rise, in each of the cases, to a sequence of the type shown in FIG. 5.

In this sequence, the first nucleotide of the sequence to be expressed comes directly after the Xa protease recognition site.

EXAMPLE 1

Design of the Vector System

Use was made of an inducible prokaryotic promoter system, i.e. the IPTG-inducible lacZ system, as is present in the vector pQE30 supplied by Qiagen. In this vector, the first protein-encoding sequence following the promoter is a sequence of 6 histidine residues. In our construct, this sequence is followed directly by a cleavage site for the Xa endoproteinase. The corresponding fifth sequence is shown in FIG. 6.

In our construct, this is then followed by a multiple cloning site which contains a BcgI recognition site. This is shown in FIG. 7.

Since a BcgI site is also present in the ampicillin resistance-encoding region of the starting vector which we used, this cleavage site, which is present in this region, was destroyed by in vitro mutagenesis while leaving the ampicillin resistance intact.

EXAMPLE 2

Cloning a foreign protein, in this case the polyoma virus structural protein VP1, into this cloning vector system.

VP1 contains a (BamHI) cleavage site which is suitable for cloning at a distance of 6 nucleotides upstream of its methionine start codon. A further, SphI, cleavage site which is required for cloning follows at a distance of 59 nucleotides after its coding sequence. The cloning vector system, as well as the construct which encompasses the VP1-encoding region, were cut with the suitable restriction endonucleases, i.e. AccI/blunt and SphI. The coding sequence was ligated into the cloning vector system which had been prepared in this way and transformed into, and amplified by growth in, *E. coli* cells (XL1 blue (lacIq), prevents expression in the absence of IPTG). Substantial quantities of the plasmid construct which had been prepared in this way were isolated and purified for further processing.

The purified construct was now digested with the enzyme BcgI, separated in an agarose gel and purified; it was then religated and once again transformed into bacteria which are particularly suitable for expression (RB791, a derivative of W3110 possessing lacIqL8), and amplified in these bacteria.

In three independent clones, it was found that the coding sequence of the VP1 protein, beginning with methionine, was located directly after the last amino acid of the factor Xa cleavage site (IleGluGlyArg)(SEQ ID NO:1).

In one clone, it was observed that, while the coding sequence of the VP1 protein followed the factor Xa sequence, the three nucleotides which encode methionine had been deleted. Similar results were obtained when the experiments were repeated with other proteins.

EXAMPLE 3

Expressing a Foreign Protein

Constructs which encoded a fusion protein containing VP1 were transformed into bacterial cells (RB79 1) and the cells were grown in an overnight culture. This overnight culture was used to grow bacterial cultures up to a density of approx. $0.8A_{600}$. Expression of the fusion protein, encompassing the histidine residues, the factor Xa recognition site and VP1, was then induced by adding IPTG. After 6 hours of induction, the total protein was harvested and an aliquot was loaded onto a gel for checking the induction efficiency. The major portion of this protein mixture was bound to a nickel chelate column in accordance with manufacturer's (Qiagen) instructions and washed on the column with various buffers. The fusion protein can be eluted from the column using a solution which contains 50 mM EGTA. However, in our case, the pure expression protein VP1 was released by subsequently digesting while adding the endoproteinase factor Xa.

SEQUENCE LISTING

```
<160> NUMBER OF SEQ ID NOS:  11

<210> SEQ ID NO 1
<211> LENGTH: 4
<212> TYPE: PRT
<213> ORGANISM: Unknown
```

-continued

```
<220> FEATURE:
<223> OTHER INFORMATION: amino-terminal 4 amino acids of the Factor
      Xa cleavage site (unknown source)

<400> SEQUENCE: 1

Ile Glu Gly Arg
  1

<210> SEQ ID NO 2
<211> LENGTH: 71
<212> TYPE: DNA
<213> ORGANISM: Unknown
<220> FEATURE:
<223> OTHER INFORMATION: nucleotide sequence from a portion of a
      vector, including part of an affinity (e.g., fusion)
      protein and a multiple cloning site (unknown source)

<400> SEQUENCE: 2
cacggatcaa tcgaaggacg catcagcctg gtccgagctg agtgcagtcg accgcatgcg      60
agctcggtac c                                                          71

<210> SEQ ID NO 3
<211> LENGTH: 7
<212> TYPE: PRT
<213> ORGANISM: Unknown
<220> FEATURE:
<223> OTHER INFORMATION: amino acid sequence encoded by the affinity
      (e.g., fusion) protein

<400> SEQUENCE: 3

His Gly Ser Ile Glu Gly Arg
  1               5

<210> SEQ ID NO 4
<211> LENGTH: 63
<212> TYPE: DNA
<213> ORGANISM: Unknown
<220> FEATURE:
<223> OTHER INFORMATION: nucleotide sequence from a portion of
      a vector, including part of an affinity (e.g., fusion)
      protein and a multiple cloning site (unknown source)
<221> NAME/KEY: misc_feature
<222> LOCATION: (1)...(63)
<223> OTHER INFORMATION: n = A,T,C or G

<400> SEQUENCE: 4
cacggatcaa tcgaaggacg catcagcctg gtccgagctg agtgcagtcg gccgcatgnn      60 nnn                                                                   63

<210> SEQ ID NO 5
<211> LENGTH: 63
<212> TYPE: DNA
<213> ORGANISM: Unknown
<220> FEATURE:
<223> OTHER INFORMATION: nucleotide sequence from a portion of a
      vector, including part of an affinity (e.g., fusion) protein
      and a multiple cloning site (unknown source)
<221> NAME/KEY: misc_feature
<222> LOCATION: (1)...(63)
<223> OTHER INFORMATION: n = A,T,C or G

<400> SEQUENCE: 5
cacggatcaa tcgaaggacg catcagcctg gtccgagctg agtgcagtcg gatccatgnn      60 nnn                                                                   63

<210> SEQ ID NO 6
```

-continued

```
<211> LENGTH: 63
<212> TYPE: DNA
<213> ORGANISM: Unknown
<220> FEATURE:
<223> OTHER INFORMATION: nucleotide sequence from a portion of a
      vector, including part of an affinity (e.g., fusion)
      protein and a multiple cloning site (unknown source)
<221> NAME/KEY: misc_feature
<222> LOCATION: (1)...(63)
<223> OTHER INFORMATION: n = A,T,C or G

<400> SEQUENCE: 6
cacggatcaa tcgaaggacg catcaccctc ctccgacctc actgcagtcg acgatatgnn      60 nnn                                                                   63

<210> SEQ ID NO 7
<211> LENGTH: 42
<212> TYPE: DNA
<213> ORGANISM: Unknown
<220> FEATURE:
<223> OTHER INFORMATION: nucleotide sequence from a portion of a
      vector, including part of an affinity (e.g., fusion) protein
      and a multiple cloning site (unknown source)
<221> NAME/KEY: misc_feature
<222> LOCATION: (1)...(42)
<223> OTHER INFORMATION: n = A,T,C or G

<400> SEQUENCE: 7
catcaccatc accatcacgg atcaatcgaa ggacgcatgn nn                         42

<210> SEQ ID NO 8
<211> LENGTH: 13
<212> TYPE: PRT
<213> ORGANISM: Unknown
<220> FEATURE:
<223> OTHER INFORMATION: amino acid sequence encoded by the affinity
      (e.g., fusion) protein

<400> SEQUENCE: 8

His His His His His His Gly Ser Ile Glu Gly Arg Met
  1               5                  10

<210> SEQ ID NO 9
<211> LENGTH: 36
<212> TYPE: DNA
<213> ORGANISM: Unknown
<220> FEATURE:
<223> OTHER INFORMATION: nucleotide sequence from a portion of a
      vector, including part of an affinity (e.g., fusion)
      protein and a multiple cloning site (unknown source)

<400> SEQUENCE: 9
catcaccatc accatcacgg atcaatcgaa ggacgc                                36

<210> SEQ ID NO 10
<211> LENGTH: 12
<212> TYPE: PRT
<213> ORGANISM: Unknown
<220> FEATURE:
<223> OTHER INFORMATION: amino acid sequence encoded by the affinity
      (e.g., fusion) protein

<400> SEQUENCE: 10

His His His His His His Gly Ser Ile Glu Gly Arg
  1               5                  10

<210> SEQ ID NO 11
<211> LENGTH: 71
```

```
<212> TYPE: DNA
<213> ORGANISM: Unknown
<220> FEATURE:
<223> OTHER INFORMATION: nucleotide sequence from a portion of a
      vector, including part of an affinity (e.g., fusion)
      protein and a multiple cloning site (unknown source)

<400> SEQUENCE: 11
cacggatcaa tcgaaggacg catcagcctg gtccgaggtg agtgcagtcg accgcatgcg     60
agctcggtac c                                                         71
``` what is claimed is:

1. A vector system for cloning comprising
   (a) a sequence encoding an affinity element,
   (b) one or more restriction endonuclease recognition sites for restriction endonucleases which cut outside their recognition sites,
   (c) one or more further restriction endonuclease recognition sites which can be used for cloning nucleic acid sequences encoding a desired foreign protein, and
   (d) a sequence encoding said foreign protein,
   wherein said restriction endonuclease recognition site(s) for restriction endonucleases which cut outside their recognition sites is/are designed such that, after restriction, the sequence encoding said foreign protein can be religated directly to said sequence encoding said affinity element.

2. The vector system of claim 1, wherein said sequence encoding said affinity element comprises an endoproteinase recognition sequence.

3. The vector system of claim 1, wherein, when several restriction endonuclease recognition sites for restriction endonucleases which cut outside their recognition sites are used, these sites are recognized by the same enzyme or by isoschizomeric enzymes.

4. The vector system of claim 1, wherein the restriction endonuclease recognition sites for restriction endonucleases which cut outside their recognition sites are two different, but ligation-compatible restriction endonuclease recognition sites.

5. The vector system of claim 1, wherein only one restriction endonuclease recognition site for restriction endonucleases which cut outside their recognition sites is present, said recognition site resulting in two cleavage sites by said restriction endonuclease.

6. The vector system of claim 5, wherein the restriction endonuclease recognition site for restriction endonucleases which cut outside their recognition sites is a recognition site for BcgI.

7. A kit for cloning foreign proteins, said kit comprising the vector system of claim 1.

8. A process for producing a desired foreign protein, said process comprising
   (a) providing the vector of claim 1,
   (b) restricting said vector with one or more of said restriction endonucleases which cut outside their recognition sites,
   (c) religating said sequence for said foreign protein directly to said fusion sequence, and
   (d) expressing a fusion protein from said vector, said fusion protein comprising said desired foreign protein.

9. The process of claim 8, wherein, after the fusion protein has been expressed, the desired foreign protein is obtained by cleaving the fusion protein at an endoprotease cleavage site which is located at the end of the fusion sequence.

10. The process of claim 9, wherein the N-terminal first amino acid is deleted from the desired foreign protein by using BcgI as the restriction endonuclease which cuts outside its recognition site.

* * * * *